(12) United States Patent
Hinds, III et al.

(10) Patent No.: US 7,229,556 B1
(45) Date of Patent: Jun. 12, 2007

(54) DELIVERY SYSTEM FOR A COMPOSITION

(75) Inventors: Bruce Jackson Hinds, III, Lexington, KY (US); Audra Lynn Stinchcomb, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 0 days.

(21) Appl. No.: 11/263,335

(22) Filed: Oct. 31, 2005

Related U.S. Application Data

(63) Continuation of application No. 11/128,443, filed on May 13, 2005.

(60) Provisional application No. 60/570,927, filed on May 13, 2004.

(51) Int. Cl.
*B01D 61/00* (2006.01)
*B01D 63/00* (2006.01)
*A61N 1/30* (2006.01)
*A61D 9/64* (2006.01)
*B01D 29/00* (2006.01)

(52) U.S. Cl. ............... 210/652; 210/500.27; 210/650; 210/257.2; 604/20; 604/21; 424/449

(58) Field of Classification Search ........... 210/500.23, 210/650, 257.2, 645, 321.8, 652; 264/29.2; 423/447.1; 424/193.1, 449; 604/305–308, 604/20–21; 428/367
See application file for complete search history.

(56) References Cited

U.S. PATENT DOCUMENTS

| | | | |
|---|---|---|---|
| 4,201,211 A | 5/1980 | Chandrasekaran et al. | |
| 5,688,524 A | 11/1997 | Hsu et al. | |
| 6,214,232 B1 * | 4/2001 | Baurmeister et al. | 210/651 |
| 6,539,250 B1 | 3/2003 | Bettinger | |
| 6,544,423 B1 * | 4/2003 | Baurmeister et al. | 210/650 |
| 6,723,077 B2 * | 4/2004 | Pickup et al. | 604/305 |
| 6,872,681 B2 * | 3/2005 | Niu et al. | 502/101 |
| 6,936,233 B2 * | 8/2005 | Smalley et al. | 423/447.1 |
| 6,949,237 B2 * | 9/2005 | Smalley et al. | 423/447.3 |
| 6,986,876 B2 * | 1/2006 | Smalley et al. | 423/447.1 |

(Continued)

OTHER PUBLICATIONS

Coralie Saby et al., "Electrochemical Modification of Glassy Carbon Electrode Using Aromatic Diazonium Salts. 1. Blocking Effect of 4-Nitrophenyl and 4-Carboxyphenyl Groups."

(Continued)

*Primary Examiner*—Ana Fortuna
(74) *Attorney, Agent, or Firm*—King & Schickli, PLLC

(57) ABSTRACT

Devices and methods for cutaneous delivery of a composition are provided, wherein the composition is passed through an ordered nanoporous membrane in fluid communication with a reservoir. The nanoporous membrane includes a plurality of aligned hollow nanotubules coated with a continuous polymer matrix, and etched to open the plurality of hollow nanotubules and form pores. In one embodiment, the etching step oxidizes an end of the nanotubules to form carboxylate groups. The ordered nanoporous membrane further includes at least one additional functional unit bound to the carboxylate groups. The at least one additional functional unit selectively exposes or at least partially occludes the pore of an adjacent nanotubule, thereby controlling flux rate through the membrane. In one embodiment, application of an electrical impulse to the membrane causes the at least one additional functional unit to selectively expose or at least partially occlude the pore.

28 Claims, 4 Drawing Sheets

U.S. PATENT DOCUMENTS

| | | | |
|---|---|---|---|
| 7,008,563 B2 * | 3/2006 | Smalley et al. | 252/511 |
| 7,011,760 B2 * | 3/2006 | Wang et al. | 210/660 |
| 7,045,205 B1 * | 5/2006 | Sager | 428/304.4 |
| 7,048,999 B2 * | 5/2006 | Smalley et al. | 428/367 |
| 7,056,455 B2 * | 6/2006 | Matyjaszewski et al. | 264/29.2 |
| 2005/0249656 A1 * | 11/2005 | Smalley et al. | 423/447.3 |

OTHER PUBLICATIONS

Langmuir 1997, 13, 6805-6813.

Jan Marwan et al. "Functionalization of Glassy Carbon Electrodes with Metal-Based Species," Chem. Mater. 2005, 17, 2395-2403.

* cited by examiner

Nicotine transport through CNT membranes

DELIVERY SYSTEM FOR A COMPOSITION

This application is a continuation of U.S. patent application Ser. No. 11/128,443 filed on May 13, 2005, which claims the benefit of Provisional Patent Application Ser. No. 60/570,927 filed on May 13, 2004, the disclosures of each of which are incorporated herein in their entirety by reference.

TECHNICAL FIELD

The present invention relates to devices and methods for cutaneous delivery of a composition. Specifically, the invention relates to devices and methods for cutaneous delivery of a composition using ordered nanoporous membranes comprising aligned nanotubules embedded in a polymer matrix. The membranes of the present invention can be functionalized for selective transport of the composition.

BACKGROUND OF THE INVENTION

Cutaneous patches, such as transdermal patches, are popular methods of non-invasive controlled release drug delivery. Additional uses of patch technology include appetite stimulation and/or suppression, for weight increase/maintenance or control. Advantages of transdermal delivery include avoidance of gastrointestinal side-effects, avoidance of the hepatic first-pass effect, maintenance of therapeutic drug levels for up to one week, reduction of drug peak-related side effects, improved patient compliance, and easy termination of drug input. Example transdermal drug delivery systems are currently available for nicotine (over the counter formulations by various manufacturers), clonidine (for example, CATAPRES), and fentanyl (for example, DURAGESIC).

Currently available transdermal delivery systems are effective for their intended purposes, but would benefit from improvements. For example, it is known that nicotine replacement smoking cessation therapy is improved by delivering nicotine at a similar rate as would be derived by smoking a cigarette, which results in peaks in plasma nicotine and improved satisfaction of cravings (Benowitz et al., Sources of variability in nicotine and cotinine levels with use of nicotine nasal spray, transdermal nicotine, and cigarette smoking, *Brit. J. of Clin. Pharm.* (1997) 43, 259-267; Russell, Nicotine replacement: the role of blood nicotine levels, their rate of change, and nicotine tolerance, In: Pomerleau et al., eds., Nicotine replacement: a critical evaluation, New York: Alan R. Liss, 1988, 187-217). However, conventional nicotine patches deliver nicotine at a constant rate resulting in steady plasma nicotine levels, and are therefore less effective (Gourlay et al., Double blind trial of repeated treatment with transdermal nicotine for relapsed smokers, *BMJ* (1995) 311, 363-6).

As another example, use of clonidine during opiate withdrawal therapy often requires an extremely complex dosing regimen. Current transdermal patch technologies cannot easily be adapted to such dosing regimens, and accordingly oral clonidine therapy is much more common. Delivery of clonidine therapy via a transdermal delivery system capable of providing a complicated, staggered dosage regimen would allow less medical supervision, decreasing health care costs. Still further, a programmable transdermal delivery system would allow flexibility in delivery and withdrawal rates for the drug, allowing flexibility in dose titration during delivery and also during withdrawal from the drug, reducing the rebound effects associated with clonidine withdrawal.

The present invention addresses the identified need in the art by providing a cutaneous delivery system for a composition, comprising an ordered nanoporous membrane and a reservoir in fluid communication with the membrane. The nanoporous membrane of the present invention can be functionalized in a variety of ways at the pore openings to impart selectivity to the membrane, to provide a selectively gateable membrane as well as other functions. A cutaneous delivery device for a composition is provided also. In one embodiment, the cutaneous delivery device is adapted to deliver the composition selectively in response to an electrical impulse.

SUMMARY OF THE INVENTION

In accordance with the purposes of the present invention as described herein, a device is provided for cutaneous delivery of a composition, comprising an ordered nanoporous membrane including a plurality of aligned hollow nanotubules and a reservoir in fluid communication with the ordered nanoporous membrane. The reservoir may be any suitable structure used as a reservoir, such as a receptacle containing the composition, a porous matrix releasably impregnated with the composition, or the like. It will be appreciated also that the composition may be provided in a variety of physical forms, including but not limited to a liquid, a gel, or any other suitable physical form. The device may further include a supplemental membrane, wherein the ordered nanoporous membrane is interposed between the reservoir and the supplemental membrane. The supplemental membrane may include, or be in contiguous contact with, a suitable adhesive for adhering the device to a surface such as skin.

The ordered nanoporous membrane may be formed by aligning the plurality of hollow nanotubules, coating the aligned hollow nanotubules with a continuous polymer matrix to form a membrane, and etching the membrane to open the plurality of hollow nanotubules and form pores. The etching step may also oxidize an end of the nanotubules to form carboxylate groups. In one embodiment, the ordered nanoporous membrane may be selectively etched to shorten the plurality of nanotubules to a length that is less than a dimension of the polymer matrix, thereby improving flux by reducing the distance traveled by the composition. Typically, the ordered nanoporous membrane is selectively etched by electrochemical oxidation, although it will be appreciated that any suitable etching technique may be utilized, with the proviso that the nanotubules are selectively shortened to a greater degree than the polymer matrix.

The ordered nanoporous membrane typically also includes at least one additional functional unit bound adjacent the nanotubule pore, which may selectively expose or at least partially occlude the pore. The additional functional unit may include at least one available amine group for binding to the nanotubule end carboxylate group. The at least one additional functional group may be selected from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, biotin, avidin, streptavidin, aliphatic amines, charged dyes, anionically charged ligands, cationically charged ligands, or any combination.

In one embodiment, the additional functional unit includes a charged group, and selectively exposes or at least partially occludes the pore of an adjacent nanotubule in response to an electrical impulse. In this embodiment, the nanotubules are typically electrically conducting and the continuous polymer matrix is typically electrically insulating, whereby the effect of the electrical impulse is substantially restricted to the plurality of nanotubules. The device may further include at least one contact in electrical communication with the ordered nanoporous membrane, and an actuator in electrical communication with the at least one contact. It will be appreciated that the actuator may be as simple as a switch for delivering an electrical impulse, or may be a programmable actuator such as a microchip, to allow initiation and termination of the electrical impulse at predetermined intervals.

In this embodiment, the additional functional unit may be selected from the group of charged groups consisting of acetate, aluminate, amino sulfonate, ammonium, quaternary ammonium, arsenate, azide, carbonate, borate, bromate, bromite, carbide, chlorite, chromate, chromite, cyanate, dichromate, phosphate, phosphite, disulfide, formate, fulminate, sulfate, sulfide, hydrogen sulfite, hydroxide, nitrate, nitrite, oxalate, pyridinium, pyrophosphate, sulfite, sulfonium, tartrate, thiocyanate, thiosulfate, toluenesulfonate, charged metal coordination compounds, or any combination thereof in accordance with the desired function. The nanotubules may be selected from the group consisting of multi-walled carbon nanotubes, single-walled carbon nanotubes, self-assembling macromolecular tubules comprising peptides and porphyrins, or any combination thereof.

In another aspect of the present invention, a method for cutaneous delivery of a composition is provided, comprising providing a reservoir containing the composition in fluid communication with an ordered nanoporous membrane comprising a plurality of hollow nanotubules and passing the composition through the ordered nanoporous membrane. As described above, the ordered nanoporous membrane may be formed by aligning the plurality of hollow nanotubules, coating the aligned hollow nanotubules with a continuous polymer matrix to form a membrane, and etching the membrane to open the plurality of hollow nanotubules and form pores. The etching step may further oxidize an end of the nanotubules to form carboxylate groups. The membrane may further be selectively etched to shorten the plurality of nanotubules to a length that is less than a dimension of the polymer matrix. Any suitable method for etching the membrane may be selected, including but not limited to electrochemical oxidation, with the proviso that the membrane is selectively etched whereby the nanotubules are shortened as noted above.

The method may further include the step of binding an additional functional unit adjacent the nanotubule pore. The additional functional unit may selectively expose or at least partially occlude the pore. Typically, functional units including an available amine group to bind to the nanotubule end carboxylate group are selected. The at least one additional functional group may be selected from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, biotin, avidin, streptavidin, aliphatic amines, charged dyes, anionically charged ligands, cationically charged ligands, and any combination thereof.

In one embodiment, the additional functional unit may include a charged group, and selectively exposes or at least partially occludes the pore of an adjacent nanotubule in response to an electrical impulse. In that embodiment, the nanotubule is typically electrically conductive, and the polymer matrix is typically electrically insulating. The additional functional unit may be selected from the group consisting of acetate, aluminate, amino sulfonate, ammonium, quaternary ammonium, arsenate, azide, carbonate, borate, bromate, bromite, carbide, chlorite, chromate, chromite, cyanate, dichromate, phosphate, phosphite, disulfide, formate, fulminate, sulfate, sulfide, hydrogen sulfite, hydroxide, nitrate, nitrite, oxalate, pyridinium, pyrophosphate, sulfite, sulfonium, tartrate, thiocyanate, thiosulfate, toluenesulfonate, charged metal coordination compounds, or combinations thereof.

The method may further include the step of providing at least one contact in electrical communication with the ordered nanoporous membrane. An actuator in electrical communication with the at least one contact may also be provided. As noted above, the actuator may be as simple as an on-off switch, or may be a programmable system such as a microchip controlling a power source.

It should be appreciated that the embodiments shown and described herein are an illustration of one of the modes best suited to carry out the invention. It will be realized that the invention is capable of other different embodiments and its several details are capable of modification in various, obvious aspects all without departing from the invention. Accordingly, the drawings and descriptions will be regarded as illustrative in nature, and not as restrictive.

BRIEF DESCRIPTION OF THE DRAWINGS

The accompanying drawings incorporated in and forming a part of the specification, illustrate several aspects of the present invention and together with the description serve to explain the principles of the invention. In the drawings.

Figure 1:
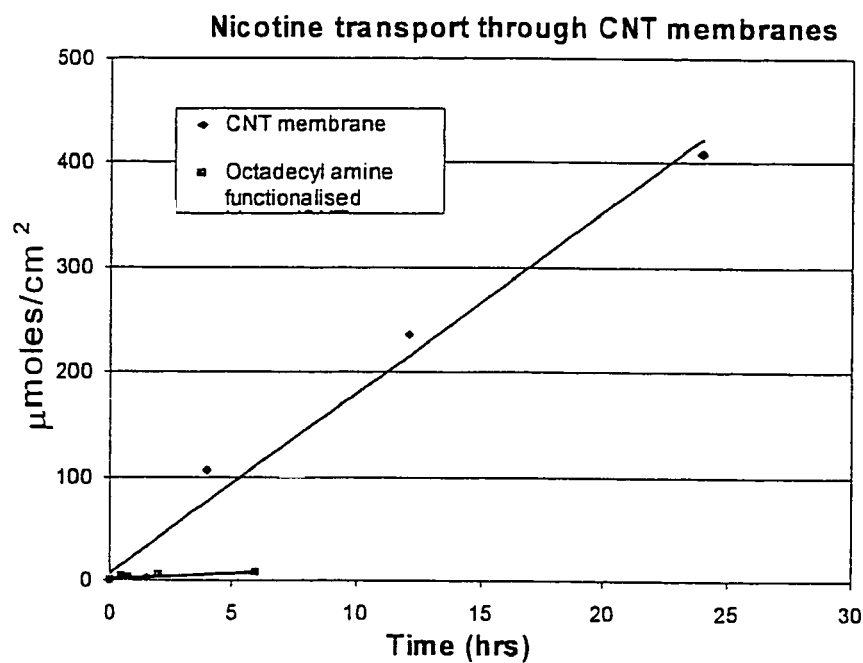
FIG. 1 shows flux of nicotine through the ordered nanotubule membrane of the present invention as a function of nanotubule tip functionalization.

Reference will now be made in detail to the present preferred embodiment of the invention, an example of which is illustrated in the accompanying drawings.

DETAILED DESCRIPTION OF THE INVENTION

The following examples are presented in support of and to further illustrate the invention as described herein. However, the invention is not to be considered as limited thereto. The patents, patent applications, and citations of literature referred to herein are understood to form a part of this disclosure, and are incorporated in their entirety by reference.

EXAMPLE 1

Ordered nanoporous membranes were prepared substantially as described in U.S. patent application Ser. No. 11/128,443, filed on May 13, 2004. Aligned carbon nanotubes (CNTs) were grown in situ using substantially the methods described in R. Andrews et al., Continuous production of aligned carbon nanotubes: a step closer to commercial realization, *Chem. Phys. Lett.* (1999) 303, 467-474, on quartz substrate using a ferrocene-xylene-argon-hydrogen feed in a chemical vapor deposition process. A 50 weight-percent solution of polystyrene (PS) and toluene was spin-coated over the surface to impregnate the CNT array. The film was dried in vacuum for 4 days, and hydrofluoric acid was then used to remove the CNT-PS composite from the quartz substrate, to produce a freestanding composite film of 5 to 10 μm thickness.

A thin layer of excess polymer from the top surface was then removed to open the CNT tips and form the pores of a membrane structure. This was accomplished with $H_2O$ plasma-enhanced oxidation process at conditions similar to conditions used to remove Fe nanocrystal catalyst particles from the CNT tips. The plasma oxidation process etched PS faster than CNTs; thus, the CNT tips were 10 to 50 nm above the polymer surface. The plasma oxidation process also left the tips of the CNTs functionalized with carboxylate groups, ready to react with amine-terminated biomolecules as will be discussed below.

The physical, chemical, and biomolecule transporting properties of the membranes are described in greater detail in U.S. patent application Ser. No. 11/128,443. As described therein, the membrane nanotubule tips of this invention can be functionalized with a variety of additional functional groups. Transport of nicotine through membranes containing non-functionalized CNT tips was compared to membranes having CNT tips functionalized with long chain alkanes. To functionalize the CNT membranes with long chain alkanes, the following conditions were used: 95.75 mg of EDC (1-ethyl-3-(3-dimethylaminopropyl) carbodiimide hydrochloride), 195.24 mg 2-(N-morpholino)ethane sulfonic acid (MES) buffer (pH 6.5), and 13.48 mg of octadecyl amine were weighed and added to 10 cc of water to make a solution having 50 mM EDC, 0.1 M MES, and 5 mM octadecyl amine. The solution was ultrasonicated for 10-15 minutes. Next, the membrane was immersed in the solution for 4 hours.

The CNT membrane was placed in a u-cell separating 10 mg/ml of nicotine in pH 7.4 buffer solution from buffered analyte solution. The concentration of nicotine in the analyte solution as a function of time was quantified by HPLC with UV detection. Analytical samples were prepared by diluting 250 μl of diffusion or standard samples in isotonic phosphate buffer pH 7.4 to 1 mL with acetonitrile. Samples were centrifuged at 3500×g for 5 min, and the supernatant was analyzed by reversed-phase HPLC (Perkin-Elmer Series 200 pump, autosampler, Brownlee Spheri5 VL C18 5 μm column with RP-18 7 μm guard column, 785A UV/VIS detector set at 259 nm, and Turbochrom 6.1.2 software). The mobile phase was acetonitrile and pH 5.5 acetate buffer (70:30). The acetate buffer was 0.05 M sodium acetate anyhydrous and 0.25% triethylamine. Flow rate was 1 ml/minute, and injection volume was 20 μl.

As shown in FIG. 1, a flux of 17 $\mu mol/cm^2 \cdot hr$ was achieved using a membrane having non-functionalized CNT tips, which compares favorably with conventional transdermal patch delivery rates of 2-6 μmol/hr for steady state delivery with increased rate requirements up to 20 μmol/hr for desired peaks in drug levels that simulate smoking. Typical transdermal patches are 5-25 $cm^2$ in size, resulting in a flexible required nicotine flux rate range of 0.08-4 $\mu mol/cm^2 \cdot hr$. This is well below published literature values for nicotine flux in human skin, as rates as high as 8.3 $\mu mol/cm^2 \cdot hr$ have been reported from 50% nicotine solutions in water [Zorin et al., In vitro test of nicotine's permeability through human skin. Risk evaluation and safety aspects, *Ann. Occup. Hyg.* 43 (1999) 405-413]. Accordingly, skin is not expected to be the rate-limiting step to transport of a composition in the present invention, but rather the ordered nanoporous membrane is expected to control the input rate.

Referring again to FIG. 1, it was shown that flux rate of nicotine through the membrane could be controllably reduced using long chain alkanes. Functionalization of the CNT tips with octadecyl amine reduced the flux rate to 2.7 $\mu mol/cm^2 \cdot hr$, or a factor of 6.2. Since the long chain amine was 2.4 nm in length, the resultant CNT pore diameter was expected to be 2.7 nm (7.5 nm–4.8 nm). The CNT cross section surface area was reduced by a factor of 7.5, which was very close to the experimentally observed flux reduction.

It will be appreciated, as discussed and described in greater detail in U.S. patent application Ser. No. 11/128,443, that the foregoing synthesis conditions are applicable to a variety of functional molecules, with the proviso that the molecule is amine-terminated to allow binding to the nanotubule carboxylate group. Accordingly, longer or shorter-chain molecules may be provided to increase or decrease flux rate as desired, by occluding the nanotubule pores to a greater or lesser degree in accordance with the properties of the composition to be transferred, such as molecular size. As described in U.S. patent application Ser. No. 11/128,443, the ordered nanoporous membrane may be selectively etched, such as by electrochemical oxidation, to reduce the length of the nanotubules to a greater degree than the width of the polymer matrix, thereby shortening the diffusion path and increasing flux rate, without compromising membrane strength or integrity.

It is common in the art to deliver certain compositions, such as drugs, via a cutaneous patch. Such patches have been found desirable for their convenience and ease of use. As examples, three skin-permeable drugs often delivered by cutaneous patch are nicotine (used in smoking cessation), fentanyl (used in pain management), and clonidine (used in opiate withdrawal and management of hypertension). The molecular weight range for nicotine, fentanyl, and clonidine is 162-336, with nicotine being the smallest and fentanyl the largest. The drugs range in lipophilicity from log octanol/water partition coefficient values of 0.88-3.62, with nicotine being the most polar and fentanyl the least. It is known that nicotine and fentanyl require fast input rates to achieve peaks in drug levels.

Conventional nicotine patches deliver 0.33 to 1 mg of nicotine per hour, meaning that the target for constant rate baseline delivery is 2-6 µmol/hr. A commercially marketed nicotine spray delivers 1 mg of drug per dose, which has a 53% bioavailability. Accordingly, a dose of 530 µg (3.3 µmol) must be delivered within a short time frame. Selecting a delivery period of 10 min as an example, the fast delivery rate for peak nicotine levels would be about 20 µmol/hr, which as seen from the foregoing disclosure is easily attained by the ordered nanoporous membrane of the present invention. Conventional nicotine transdermal patches are 5-25 $cm^2$ in size, resulting in a flexible required nicotine flux rate range of 0.08-4 µmol/$cm^2$·hr. Skin is unlikely to be a rate-limiting factor, as flux rates as high as 8.3 µmol/$cm^2$ hr have been reported from 50% nicotine solutions in water (Zorin et al., 1999). Accordingly, the ordered nanoporous membrane of the present invention can be expected to reliably control the nicotine drug input rate to the body.

An example dynamic dosing regimen for oral clonidine during opiate withdrawal therapy is: 0.1 mg twice daily on day 1, thrice daily on day 2, and four times daily on days 3 and 4, thrice daily on days 5 and 6, twice daily on days 7 and 8, and once daily on days 9 and 10. The oral bioavailability of clonidine is 90% or less (decreased bioavailability with multiple dosing), so the required transdermal regimen can be expected to be 0.18 mg/d on day one, to a maximum rate of 0.36 mg/d, and then down to 0.09 mg/d by the end of the treatment period [Frisk-Holmberg et al., Clonidine kinetics in man-evidence for dose dependency and changed pharmacokinetics during chronic therapy, *Brit. J. Clin. Pharm.* 12 (1981) 653-658]. A currently marketed lowest dose clonidine patch delivers 4.32 µg/h from a 3.5 $cm^2$ patch, or 1.2 µg/$cm^2$·hr [Toon et al., Rate and extent of absorption of clonidine from a transdermal therapeutic system, *J. Pharm. and Pharmacol.* 41 (1989) 17-21]. Flux values for clonidine in human skin are reported as high as 3.3 µg/$cm^2$·hr [Wang et al., Permeation studies of clonidine through skins and different artificial membranes, *Zhongua Yaoxue Zazhi* 45 (1993) 591-600]. Assuming a 10 $cm^2$ patch, the required delivery rate range for a transdermal patch would be 0.375 to 1.5 µg/$cm^2$·hr to ensure that the skin would not rate-limit the drug delivery. Again, this delivery rate is well within the delivery rate ranges achievable using the nanoporous ordered membrane of the present invention.

As another example, commercially available fentanyl patches used in pain management deliver constant rates of 25 to 100 µg/hr. The lag time across human skin is 12 minutes, which is important for the breakthrough pain treatment increase in delivery rates [Roy et al., Transdermal delivery of narcotic analgesics: pH, anatomical, and subject influences on cutaneous permeability of fentanyl and sufentanil, *Pharm. Res.* 7 (1990) 842-847]. Breakthrough cancer pain can be treated with a fentanyl nasal spray at a dose of 20 µg, which results in analgesia within 10 minutes [Zeppetella, G., An assessment of the safety, efficacy, and acceptability of intranasal fentanyl citrate in the management of cancer-related breakthrough pain: a pilot study, *J. Pain and Symptom Management* 20 (2000) 253-258]. Breakthrough cancer pain is often treated with a 200 µg fentanyl lozenge (ACTIQ®) in patients already under treatment with opioids. The buccal bioavailability of this fentanyl lozenge is 50%, so the delivery of 100 µg over 10 minutes would be a reasonable transdermal delivery goal for pain bouts (0.6 mg/$cm^2$·hr). Maximum flux rates of fentanyl across human skin have been reported at 2.6 mg/$cm^2$·hr [Roy et al., 1990; Michaels et al., *AIChE* 21 (1975) 985-996].

The ordered nanoporous membrane of the present invention was shown to provide a delivery rate for a composition well within the necessary ranges for such compositions as nicotine, clonidine, and fentanyl in accordance with information derived from delivery rates of conventional cutaneous patches. Attention was therefore turned to adapting the ordered nanoporous membrane for use as a component of a cutaneous patch.

EXAMPLE 2

Consideration was given to supplemental membranes for use as components of cutaneous delivery systems in combination with the ordered nanoporous membranes of the present invention. Potentially suitable polymer films and pressure sensitive adhesives were evaluated to define polymer/adhesive combinations providing the least diffusional resistance. Four commercially-available polymer membranes and three pressure sensitive adhesives were considered. The four membranes evaluated were: (1) a copolyester membrane (MEDIFILM® 390; Mylan Technologies, Inc., St. Albans, VT); (2) a polyurethane membrane (MEDIFILM® 437); (3) an ethyl vinyl acetate membrane (MEDIFILM® 500); and (4) a polyether block amide membrane (MEDIFILM® 840). The adhesives evaluated were: (1) an acrylic pressure sensitive adhesive having no functional groups to prevent chemical interaction of drugs with adhesive polymer (DURO-TAK® 87-900A, National Starch & Chemical Co., Bridgewater, N.J.); a silicone pressure sensitive amine-compatible adhesive (BIO-PSA® 7-4303, Dow Corning Co., Midland, Mich.); and (3) a silicone pressure sensitive standard adhesive (BIO-PSA® 7-4606, Dow Corning).

The adhesives were adhered to the different polymer membranes, and the adhesive/polymer combination was pressed onto pieces of hairless guinea pig skin. Skin samples were also tested with the same drug solution without adhesive/polymer combinations. The membrane composites were placed into flow-through PermeGear diffusion cells at 32° C. (n=3), and nicotine in phosphate buffer was applied to the polymer surface. Experiments were run for a 24 hr period with a receiver solution of isotonic phosphate buffer solution pH 7.4 at a flow rate of 5 mL/hr. Samples were collected every 3 hr using a fraction collector. Nicotine concentration in collected samples was determined by HPLC as described in Example 1. Results are presented in Table 1.

TABLE 1

Nicotine flux rates for combinations of polymer membranes and pressure sensitive adhesives.

| Polymer membrane/adhesive | Flux rate (µmol/$cm^2$.hr) |
| --- | --- |
| MEDIFILM ® 840/DURO-TAK ® 87-900A | 19.3 ± 2.9 |
| MEDIFILM ® 840/BIO-PSA ® 7-4303 | 9.7 ± 2.2 |
| MEDIFILM ® 500/BIO-PSA ® 7-4303 | 8.7 ± 6.2 |
| MEDIFILM ® 390/BIO-PSA ® 7-4303 | 17.2 ± 4.9 |
| MEDIFILM ® 437/BIO-PSA ® 7-4303 | 12.1 ± 0.9 |
| MEDIFILM ® 437/BIO-PSA ® 7-4606 | 18.8 ± 5.1 |
| Skin only | 31.4 ± 9.3 |

These results indicated that the combinations of a polyether block amide membrane/acrylic pressure sensitive adhesive without functional groups, polyether block amide membrane/silicone pressure sensitive amine-compatible adhesive, and polyurethane membrane/silicone pressure sensitive standard adhesive provided acceptable flux rates for nicotine. However, it was noted that all polymer membranes evaluated provided flux rates for nicotine that were well in excess of the maximum required delivery rate of 4 µmol/cm²·hr as has been found desirable in a conventional nicotine cutaneous patch as previously discussed. Therefore, the supplemental polymer membranes are not expected to contribute appreciably to variation in flux rate.

It will be appreciated also by the skilled artisan that the selection of combinations of polymer membranes/adhesives for use in a cutaneous delivery system will be dictated by the properties of the compositions to be passed therethrough, i.e., by the desired flux rate for the particular compositions, the propensity of the composition to interact with the polymer and/or the adhesive, and the like. Such evaluations are well within the knowledge possessed by the skilled artisan.

EXAMPLE 3

Next, a delivery system adaptable for cutaneous delivery was evaluated, comprising the ordered nanoporous membrane of Example 1 as the rate-controlling component and the polymer/adhesive supplemental membrane of Example 2 as a protective mechanism to reduce risk of biofouling of the ordered nanoporous membrane. A non-functionalized CNT membrane prepared substantially as described in Example 1 was adhered to MEDIFILM® 840 using DURO-TAK® 87-900A. The composite membrane was placed into a flow-through diffusion cell and evaluated for nicotine transport as described in Example 2. Polymer/skin patches (without CNT membranes) were used as controls.

Figure 2:
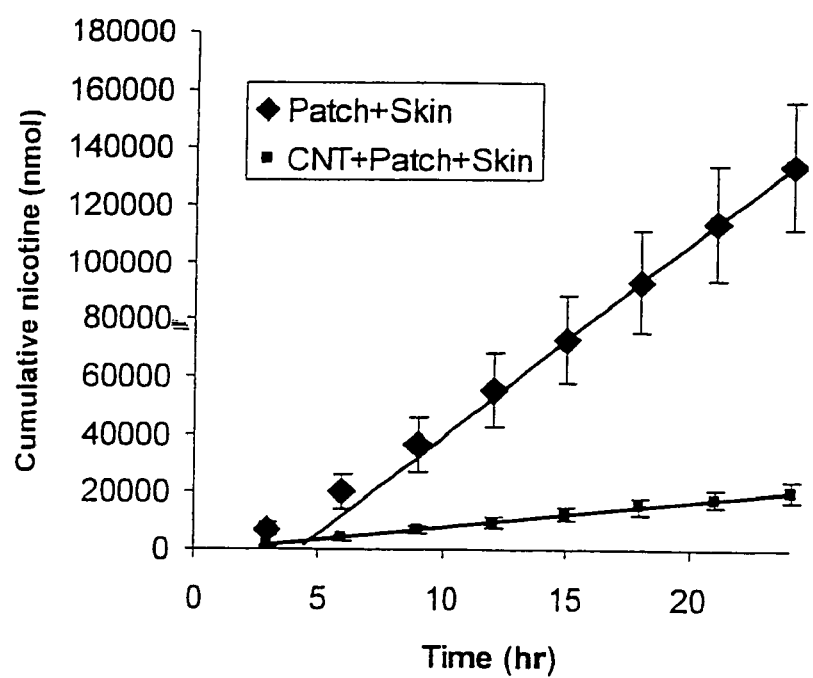
FIG. 2 shows flux of nicotine through a polymer membrane/skin composite with and without the ordered nanotubule membrane of the present invention.

As shown in FIG. 2, the nicotine flux from the CNT membrane/polymer membrane/skin patches was 8-fold less than nicotine flux from the polymer membrane/skin patches. A good linear steady-state diffusion profile was obtained with the CNT membrane/polymer membrane/skin patches over a 24 hr period, and the membrane was intact and undamaged at the end of the experiment (not shown). Nicotine flux from the membrane was 0.90 µmol/cm²·hr, well within a desirable delivery range for nicotine of 0.08-4 µmol/cm²·hr.

Accordingly, the present work demonstrates that the ordered nanoporous membranes of this invention can be adapted as components of a patch for delivery of a composition to a surface such as skin. It will be appreciated that, based on known physicochemical properties of compositions adaptable for delivery by a cutaneous patch, properties of the patches can be optimized for specific delivery rates of the drug of choice. In cases where the flux value for a particular composition intended to be provided as a transdermal formulation is less than desired for a predetermined transdermal delivery rate, penetration enhancers such as ethanol, oleic acid, or other surfactants may be added to the compositions to improve delivery rate.

For complicated dosage regimens such as that described herein for clonidine, and also for intermittent dosage regimens for drugs such as nicotine or fentanyl wherein it is desired to provide drug delivery "peaks" interspersed with intervening periods of reduced or no drug delivery (to address intermittent events such as nicotine craving or breakthrough pain, for example), it is desirable to adapt a cutaneous delivery system as described in the foregoing disclosure for selective delivery of a composition, rather than constant delivery at a predetermined flux rate over time.

To address this need, a gateable ordered nanoporous membrane is provided herein, wherein the pores of the membrane can be selectively exposed or occluded.

Figure 3:
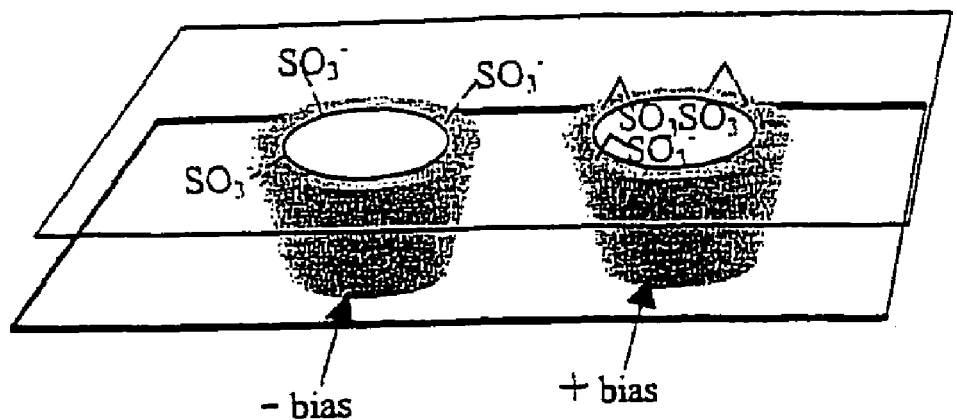
FIG. 3 schematically depicts the opening and closing of nanotubule pores by a charged functional group (amino sulfonate) using application of a positive or a negative bias.

The nanotubules forming the membrane pores may be functionalized at the tip with charged functional groups. As has been previously described (U.S. patent application Ser. No. 11/128,443), in the embodiment of the ordered nanotubule membrane of the present invention comprising aligned carbon nanotubes in a polymer matrix (Example 1), the carbon nanotubes are conductive, while the polymer matrix (in the described embodiment, polystyrene) may be insulating. It will be appreciated that placing a charged functional group adjacent to the nanotubule pore (attached thereto by the same amide chemistry as previously described herein, see Example 1, or by any other suitable method) allows use of electrostatic capacitance to draw the charged group towards the conductive nanotubule wall or to repel the charged group therefrom, occluding or exposing the nanotubule pore as shown schematically in FIG. 3. Of course, the electrical impulse applied will be either a negative bias or a positive bias, depending on whether the charged functional group used is positively or negatively charged, to achieve the desired attraction or repulsion from the nanotubule wall.

Because the polymer matrix is insulating, the applied bias or electrical impulse would be applied only to the nanotubule. This provides the further benefit of being able to isolate the applied electrical impulse to the pores of the ordered nanoporous membrane, rather than to the entirety of the membrane and/or the surface to which the composition is to be delivered. This phenomenon is often seen with conventional non-invasive programmable drug delivery methods such as iontophoresis, electroporation, and the like, resulting in undesirable skin irritation and/or disruption of the skin barrier.

EXAMPLE 4

Figure 4:
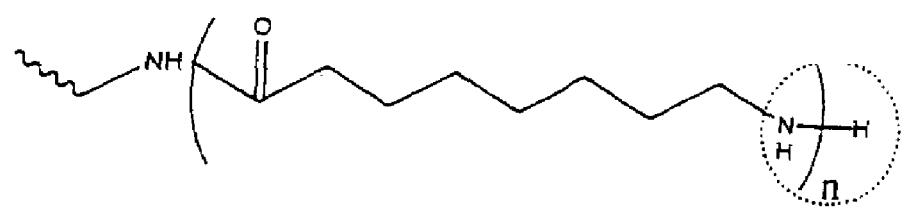
FIG. 4 schematically depicts a tether molecule comprising a series of polypeptide links, wherein length is controlled by successive carboimide reactions at a nanotubule (n) pore.

An ordered nanotubule membrane was fabricated substantially as described in Example 1, for use in evaluation of use of charged molecules for selective exposing/occlusion of the pores of the membrane. A polypeptide tether (see FIG. 4) was used to bond charged dye molecules (Direct Blue 71; Aldrich) adjacent the nanotubule pores using the carboimide chemistry substantially as described herein and in U.S. patent application Ser. No. 11/128,443. Briefly, dye was added to a 4 ml solution of 0.1 M MES to make a 50 mM solution. Eight mg of 1-[3-(Dimethylamino)propyl]-3ethyl-carbodiimide hydrochloride (EDC) was dissolved in the solution, followed by immersion of the nanotubule membrane therein. The reaction proceeded for 12 hr at ambient temperature, followed by washing with MES buffer and isopropyl alcohol to remove excess reagents.

Flux through the functionalized membrane was evaluated using a U-tube permeation experiment substantially as described in Example 1. Liquids in the two chambers of the permeation set-up were maintained at the same level to prevent pressure-induced transport. Methyl viologen dichloride hydrate (methylviologen$^{2+}$; Aldrich) was the probe molecule. The permeate was periodically pipetted out, tested for presence of probe molecule by UV-vis spectroscopy (HP 8543 Spectrophotometer), and then transferred back to the chamber. A peak detected at 260 mm was used to quantify the amount of methylviologen$^{2+}$. A calibration curve was determined by fitting non-linear (to account for the non-linear deviation from Lambert-Beer's Law in higher concentrations of analyte) curves to plots of absorbance vs. concentration of the analyte in the range $5*10^{-4}$ (M) to $1*10^{-6}$ (M).

Figure 5:
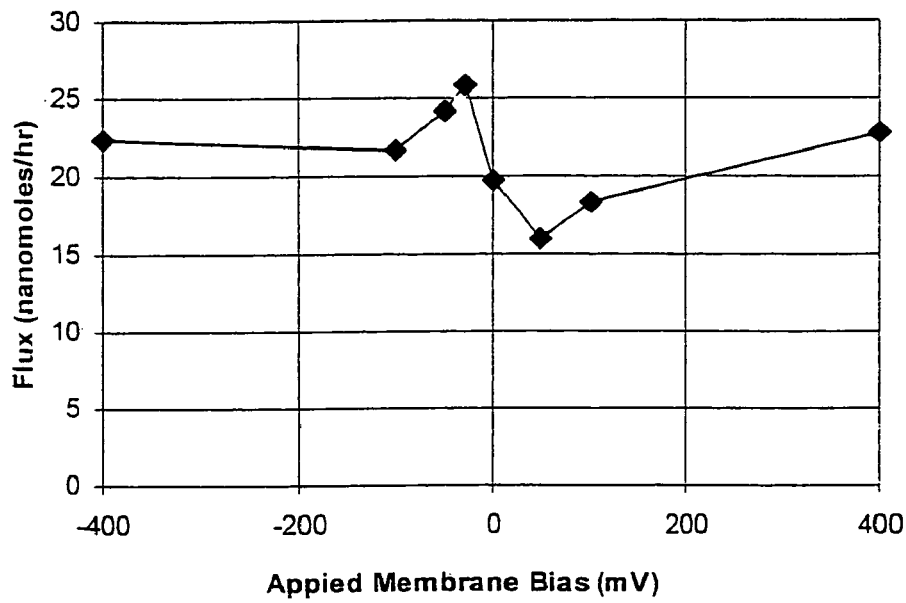
FIG. 5 shows transport of methylviologen$^{2+}$ across a nanotubule membrane functionalized with anionic dye coupled to a tether molecule (see FIG. 4) consisting of 2 polypeptide links.

As shown in FIG. 5, the flux of methylviologen$^{2+}$ through the functionalized nanotubule membrane was altered by application of an electrical impulse to the dye/polypeptide functionalized nanotubule membrane. A 60% increase in flux was observed from a bias of +50 mV to −30 mV (0.1 M KCl electrolye), clearly demonstrating that the applied bias modulated chemical flux through the membrane of the present invention.

EXAMPLE 5

Figure 6:
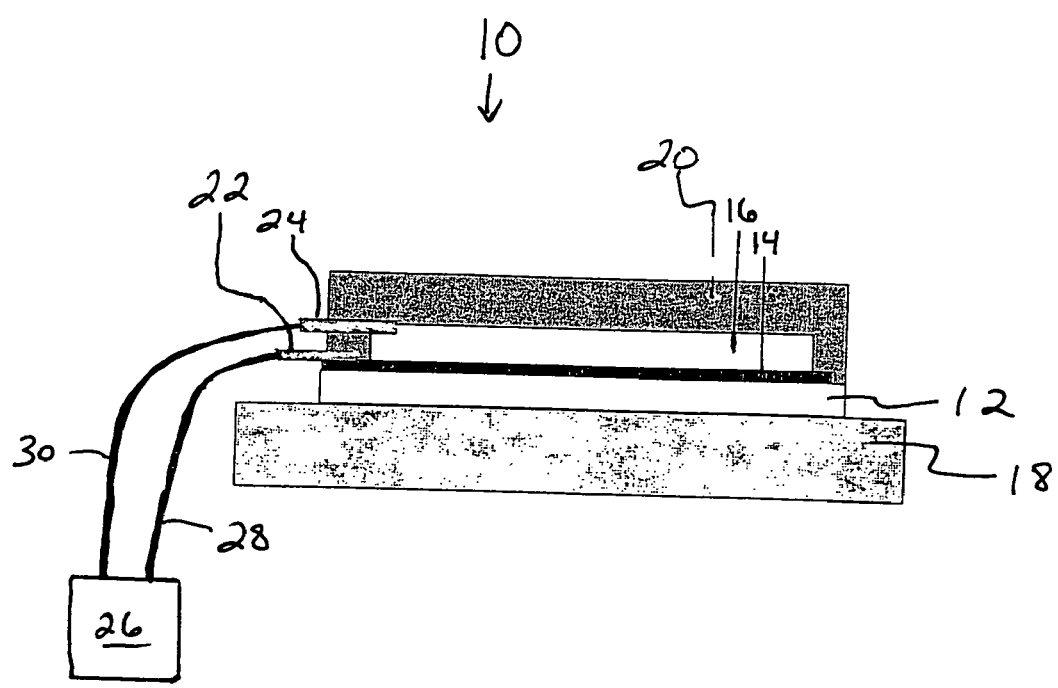
FIG. 6 schematically depicts an embodiment of a cutaneous delivery system, wherein delivery of a composition is effected by application of an electrical impulse.

Referring now to FIG. 6, a selectively gateable delivery system 10 is depicted wherein the nanotubule pore of the ordered nanoporous membrane is selectively exposed or at least partially occluded by application of an electrical impulse (applied bias) as described in Example 4. The delivery system 10, in this embodiment adapted for use as a cutaneous delivery system, comprises a supplemental polymer membrane 12, a nanotubule membrane 14 (see Example 1) adhered to the polymer membrane 12, a reservoir 16 for holding a composition for delivery to a skin surface 18, and a cover 20. Any suitable fastener or restraint for maintaining contact between the delivery system 10 and an adjacent surface may also be provided, such as an adhesive, an elastic loop, ring, or band, fastening tape, a strap, a buckled strap, a tie, a band secured by hook and loop material, and the like. For example, the polymer membrane 12 may optionally include a pressure sensitive adhesive (see Example 2) on a margin thereof to maintain the delivery system 10 in contact with a surface such as skin.

A first contact 22 is placed in electrical communication with the nanotubule membrane 14, and a second contact 24 is placed in electrical communication with the reservoir 16. An actuator 26 is provided also, in electrical communication with the first and second contacts 22, 24 via leads 28, 30.

The cover 20 may be fabricated of any suitable material providing the desired protective effect. Typically, the cover 20 will be fabricated of a breathable material, which prevents entry of water but allows escape of water vapor such as perspiration, to improve user comfort. The actuator 26 may be as simple as a power source (not shown) having a switch for allowing transmission of an electrical current to the nanotubule membrane 14, or may comprise more complex control electronics. Suitable actuators by which programmable activation/deactivation of the delivery system can be achieved are known in the art. For example, the actuators described in U.S. Pat. Nos. 6,539,250 and 6,723, 077, the disclosures of which are incorporated herein in their entirety by reference, can be adapted for use in the present invention. As noted above, the nanotubules of the membrane are typically electrically conductive, whereas the polymer matrix is typically electrically insulating. Accordingly, the delivery system allows isolation of the applied electrical impulse to the nanotubule array of the ordered nanoporous membrane, reducing the likelihood of skin irritation, disruption of the skin barrier, and other similar undesirable effects.

The skilled artisan will quickly appreciate that the cutaneous delivery system described herein can be easily modified for optimal delivery of a variety of compositions, based on known physicochemical properties of the composition to be delivered. Particular emphasis is placed on the role of ionic strength for aqueous solutions placed in the reservoir 16. Alternatively, non-polar solvents commonly used in transdermal systems can be used for delivery of the compositions, such as mineral oil, propylene glycol, and ethanol. Since the membrane of the present invention has a surface resistance of 0.32/Ωcm, it is well within the knowledge expected of the skilled artisan to determine the optimal ionic strength of the composition reference solution to find a threshold concentration for ionic interference in an aqueous solution.

The required bias to attract charged groups into the nanotubule pores for occlusion thereof can also be estimated from electrochemical studies of long-chained charged functional group (1-thioundecanecarboxylic acid) monolayers on gold electrodes [Krishna et al., Tethered bilayer membranes containing ionic reservoirs: The interfacial capacitance, *Langmuir* 17 (2001) 4858-4866]. Interfacial capacitances have been experimentally measured at from 2.4 μF/cm$^2$ to 1.6 μF/cm$^2$ for solutions of 1 to 1000 mM ionic strength (NaCl). For nanotubule membranes comprising vertically aligned carbon nanotubes (Example 1) having approximately 20 charged functional groups per carbon nanotube ($1\times10^{12}$/cm$^2$) the required bias is 67-100 mV, which is well within practical limitations.

The structure of the double charge layer is largely determined by Helmholtz capacitance and the Debye screening length. Mobile ions in solution can reach the interface and effectively screen the charge on the electrode from the charged functional group at the end of the tethered functional molecule (2-3 nm long). The Debye screening length in solution is given by the formula:

$$\lambda_d = \sqrt{8\pi \frac{e^2}{k_b T \varepsilon_r \varepsilon_o} C_s}$$

where $\varepsilon_r$ is the relative dielectric constant of solvent ($\varepsilon_r \sim 80$ for H$_2$O), T=temperature in Kelvin, $k_b$=Boltzman constant, and $C_s$ is ionic concentration in solution.

In vivo ionic strengths (0.15M) have a Debye length of 0.8 nm, which is shorter than the length of the tethered molecule, and therefore ionic interference can be expected to be a variable to be considered. For a 0.01M solution the Debye length is an acceptable 3 nm. Using a mineral oil solvent can be expected to reduce $\varepsilon_r$ to approximately 3, and $C_s$ to approximately mM, and accordingly net Debye screening lengths would be approximately 50 nm. This is well beyond the length of the tethered molecule, and ionic screening would not be expected to be a factor when using non-aqueous solvents currently used for transdermal cutanous patches. The Debye screening length is actually an upper limit of ionic interference, since studies with polyelectrolyte brushes predict significant contraction in 0.1 M ionic strength solutions under applied bias using a modified Gouy-Chapman length model [Zhulina et al., Screening effects in a polyelectrolyte brush: Self-consistent-field-theory, *Macromolecules* 33 (2000) 4945-4953]. By varying ionic strength and $\varepsilon_r$ of the aqueous solution, the present invention can easily be tailored for use of aqueous solvents without ionic interference.

It will be appreciated by the skilled artisan that the carboimide chemistry described in the foregoing disclosure can be used to attach a variety of charged functional molecules adjacent the nanotubule pores of the ordered nanoporous membrane of the present invention, for use as "gate-keeper" molecules in devices such as a cutaneous patch as described in Examples 4 and 5. Alternatively, as discussed supra other suitable methods for binding functional molecules adjacent the nanotubule pores may be employed, such as electrochemical modification. The proviso is that the molecule must be amino-terminated, and must have a charged moiety which causes the molecule to selectively expose or at least partially occlude the adjacent pore in response to an applied bias. Examples include, but are not limited to, amino sulfonates, charged triphenylphosphonium, and thiol-gold nanocrystal molecules. Polypeptide tethers may be fabricated using carboimide chemistry to increase the length of the charged molecule/tether composite as desired.

EXAMPLE 6

An ordered nanoporous membrane is synthesized substantially as described in Example 1. A commercially available long chain amino sulfonate (FIG. 7a) is attached to a carboxylate group at a nanotubule pore by the depicted amino group using the carboimide chemistry described in Example 1.

EXAMPLE 7

An ordered nanoporous membrane is synthesized substantially as described in Example 1. A commercially available short chain amino sulfonate (FIG. 7b) is attached to a carboxylate group at a nanotubule pore by the depicted amino group using the carboimide chemistry described in Example 1.

EXAMPLE 8

An ordered nanoporous membrane is synthesized substantially as described in Example 1. Chain lengths are added to charged triphenylphosphonium by acidic deprotection of cyclic acetyl group and reaction with n-amino bromo alkane (FIG. 7c), and the molecule is attached to a carboxylate group at a nanotubule pore by the depicted amino group using the carboimide chemistry described in Example 1.

EXAMPLE 9

Figure 7A:
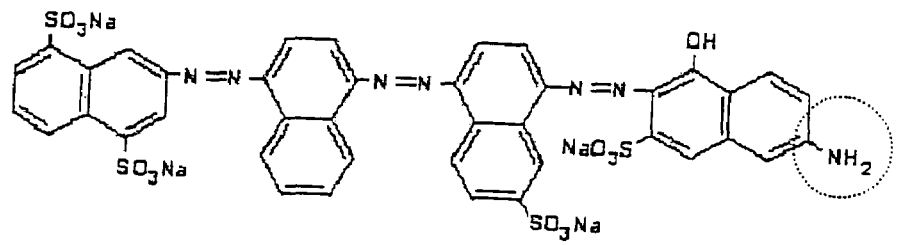
FIG. 7 schematically depicts various molecules useful in functionalizing the ordered nanoporous membrane of the present invention with charged molecules: (7a) long chain amino sulfonate; (7b) short chain amino sulfonate; (7c) schematic depiction of a charged triphenylphosphonium molecule having added chain lengths; (7d) schematic depiction of attachment of a charged thiol-gold nanocrystal molecule.
Figure 7B:
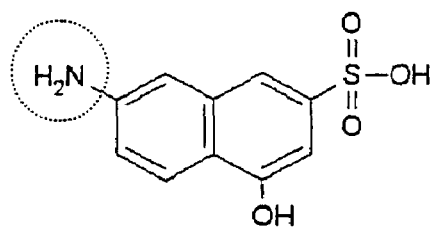
Figure 7C:
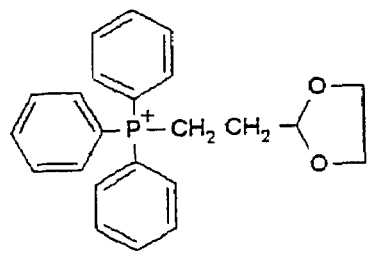

An ordered nanoporous membrane is synthesized substantially as described in Example 1. A polypeptide tether (FIG. 4) is attached to a carboxylate group at a nanotubule pore by the depicted amino group using the carboimide chemistry described in Example 1. Length of the polypeptide tethers is increased as desired by successive carboimide reactions at a nanotubule (n) entrance. Polypeptide tether length is controlled by the number of times the terminal carboxylate on the nanotubule (n) is activated by EDC coupling agent, followed by placement in 8-amino caprylic acid (ACA) solution. Charged molecules such as those depicted in FIGS. 7a-c are coupled to the polypeptide tethers using the same carboimide chemistry as previously described.

EXAMPLE 10

Figure 7D:
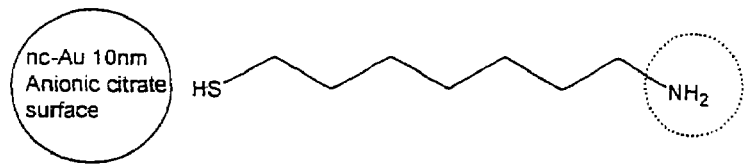

Referring to FIG. 7d, a charged molecule is attached to a nanotubule pore carboxylate group by addition of a thiol (SH) group, followed by covalent bonding to a gold nanocrystal. Gold nanocrystals are normally anionically charged to be a stable colloidal system, and therefore the molecule's position at the nanotubule pore entrance can be altered from an occluding position to an open position by electrostatic force.

The foregoing description of the preferred embodiment of this invention has been presented for purposes of illustration and description. It is not intended to be exhaustive or to limit the invention to the precise form disclosed. Obvious modifications or variations are possible in light of the above teachings. For example, the method of providing an aligned array of hollow nanotubules is not limited to the example described in Example 1. Any suitable method for providing an aligned array of nanotubules may be employed, such as for example embedding nanotubules such as carbon nanotubes in a porous alumina template. It is also known to grow carbon nanotubes or other self-assembling nanotubules in situ in a porous template such as alumina.

Similarly, the additional functional group may be bound adjacent the nanotubule pore of the ordered nanoporous membrane by alternative methods, with the proviso that the functional groups bind only near the nanotubule tips, rather than binding further into the interior of the nanotubule lumen. For example, it is known to electrochemically modify graphitic surfaces to allow binding of functional groups. Saby et al. demonstrated electrochemical reduction of substituted (using a para substituent such as nitro, carboxy, etc.) phenyl diazonium to form a diazonium radical, covalently binding to the surface of a glassy carbon electrode, and grafting a correspondingly substituted phenyl group [see Saby et al., Electrochemical Modification of Glassy Carbon Electrode Using Aromatic Diazonium Salts. 1. Blocking Effect of 4-Nitrophenyl and 4-Carboxyphenyl Groups, *Langmuir* 13, p. 6805-6813 (1997)].

Marwan et al. demonstrated electrochemical grafting of N,N-Diethylaniline to a glassy carbon electrode, followed by binding a charged copper molecule or Prussian Blue dye, as well as modification of a glassy carbon electrode with 4-sulfonate phenyl and binding of charged ruthenium [Marwan et al., Functionalization of glassy carbon electrodes with metal-based species, *Chem. Mater.* 17, pp. 2395-2403 (2005)]. It will be appreciated that, for example, the ordered nanoporous membranes of the present invention comprising carbon nanotubes could be similarly modified to bind functional groups. Because only the tips of the carbon nanotubes extend beyond the surface of the matrix in which they are embedded, functional groups would bind only to the nanotube tips, and therefore only adjacent the membrane pores.

The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A device for cutaneous delivery of a composition, comprising:
   an ordered nanoporous membrane including a plurality of aligned hollow nanotubules held in a continuous polymer matrix, the plurality of aligned hollow nanotubules having a lumen defining at least one pore passing through the ordered nanoporous membrane; and
   a reservoir for holding the composition, said reservoir in fluid communication with the ordered nanoporous membrane.

2. The device of claim 1, wherein the ordered nanoporous membrane includes at least one functional unit bound adjacent to the pore.

3. The device of claim 2, wherein the at least one functional unit selectively exposes or at least partially occludes the pore of an adjacent nanotubule.

4. The device of claim 3, wherein the at least one functional unit is selected from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, biotin, avidin, streptavidin, aliphatic amines, charged dyes, anionically charged ligands, cationically charged ligands, and any combination thereof.

5. The device of claim 3, wherein the at least one functional unit is selectively displaceable to at least partially expose or at least partially occlude the pore of an adjacent nanotubule.

6. The device of claim 5, wherein the at least one functional unit includes a charged group.

7. The device of claim 6, wherein the at least one functional unit is selected from the group of charged groups consisting of acetate, aluminate, amino sulfonate, ammonium, quaternary ammonium, arsenate, azide, carbonate, borate, bromate, bromite, carbide, chlorite, chromate, chromite, cyanate, dichromate, phosphate, phosphite, disulfide, formate, fulminate, sulfate, sulfide, hydrogen sulfite, hydroxide, nitrate, nitrite, oxalate, pyridinium, pyrophosphate, sulfite, sulfonium, tartrate, thiocyanate, thiosulfate, toluenesulfonate, charged metal coordination compounds, and any combination thereof.

8. The device of claim 6, wherein the continuous polymer matrix is electrically insulating.

9. The device of claim 6, wherein the aligned hollow nanotubules are electrically conductive.

10. The device of claim 5, further including at least one contact in electrical communication with the ordered nanoporous membrane.

11. The device of claim 10, further including an actuator in electrical communication with the at least one contact.

12. The device of claim 1, wherein the nanotubules are selected from the group consisting of multi-walled carbon nanotubes, single-walled carbon nanotubes, self-assembling macromolecular tubules comprising peptides and porphyrins, and any combination thereof.

13. The device of claim 1, further including a fastener for holding the device adjacent to a surface.

14. The device of claim 13, wherein the fastener is selected from the group consisting of an adhesive, a pressure sensitive adhesive, an elastic band, loop, or ring, a hook and loop material, a tape, a strap securable by adhesive, hook and loop material, or a buckle, a tie, and any combination thereof.

15. A method for cutaneous delivery of a composition, comprising:
providing a reservoir containing the composition in fluid communication with an ordered nanoporous membrane comprising a plurality of hollow nanotubules held in a continuous polymer matrix, the plurality of hollow nanotubules having a lumen defining at least one pore passing through the ordered nanoporous membrane; and
passing the composition through the ordered nanoporous membrane.

16. The method of claim 15, wherein the ordered nanoporous membrane is formed by aligning the plurality of hollow nanotubules, coating the aligned hollow nanotubules with the continuous polymer matrix to form a membrane, and etching the membrane to open the plurality of hollow nanotubules and form pores.

17. The method of claim 16, further including the step of binding at least one functional unit adjacent to the nanotubule pore.

18. The method of claim 17, wherein the at least one functional unit selectively exposes or at least partially occludes the pore of an adjacent nanotubule.

19. The method of claim 18, including selecting the at least one functional unit from the group consisting of a ligand, a receptor, a receptor-ligand complex, a reversibly binding receptor-ligand complex, a charged molecule, a binder-ligand complex, a reversibly binding binder-ligand complex, a ligand adapted for specifically binding to a predetermined target molecule, a hydrophilic molecule, a hydrophobic molecule, a catalytic coordination compound, a catalytic metal, biotin, avidin, streptavidin, aliphatic amines, charged dyes, anionically charged ligands, cationically charged ligands, and any combination thereof.

20. The method of claim 18, wherein the functional unit is selectively displaceable to at least partially expose or at least partially occlude the pore of an adjacent nanotubule.

21. The method of claim 20, including selecting a functional unit having a charged group.

22. The method of claim 21, including selecting the at least one functional unit from the group consisting of acetate, aluminate, amino sulfonate, ammonium, quaternary ammonium, arsenate, azide, carbonate, borate, bromate, bromite, carbide, chlorite, chromate, chromite, cyanate, dichromate, phosphate, phosphite, disulfide, formate, fulminate, sulfate, sulfide, hydrogen sulfite, hydroxide, nitrate, nitrite, oxalate, pyridinium, pyrophosphate, sulfite, sulfonium, tartrate, thiocyanate, thiosulfate, toluenesulfonate, charged metal coordination compounds, and any combination thereof.

23. The method of claim 21, further including the step of providing at least one contact in electrical communication with the ordered nanoporous membrane.

24. The method of claim 23, further including the step of providing an actuator in electrical communication with the at least one contact.

25. The method of claim 21, wherein the plurality of aligned hollow nanotubules are electrically conductive.

26. The method of claim 21, wherein the continuous polymer matrix is formed of an electrically insulating polymer.

27. The method of claim 16, further including the step of providing a fastener for holding the ordered nanoporous membrane adjacent to a surface.

28. A device for cutaneous delivery of a composition, comprising:
an ordered nanoporous membrane including a plurality of aligned hollow nanotubules held in a continuous polymer matrix; and
a reservoir for holding the composition, said reservoir in fluid communication with the ordered nanoporous membrane;
wherein the ordered nanoporous membrane further includes at least one functional unit bound adjacent to a pore defined by a lumen of the hollow nanotubule.

* * * * *